United States Patent [19]

Kollonitsch et al.

[11] 4,347,374

[45] Aug. 31, 1982

[54] ACID ADDITION SALTS OF N-TRITYL-α-FLUOROMETHYLHISTIDINE ENANTIOMER DERIVATIVES

[75] Inventors: Janos Kollonitsch, Westfield; Leroy M. Perkins, Metuchen; George A. Doldouras, Fanwood; Stephen Marburg, Metuchen, all of N.J.

[73] Assignee: Merck & Co., Inc., Rahway, N.J.

[21] Appl. No.: 170,398

[22] Filed: Jul. 21, 1980

[51] Int. Cl.³ ............................................. C07D 233/64
[52] U.S. Cl. .................................................... 548/344
[58] Field of Search ........................................ 548/344

[56] References Cited

U.S. PATENT DOCUMENTS 4,288,601  9/1981  Kollonitsch et al. ............... 548/344

FOREIGN PATENT DOCUMENTS 867702   1/1978  Belgium .
2001626  2/1979  United Kingdom .

OTHER PUBLICATIONS

Yamada et al., Chem. Abst. 1979, vol. 91, No. 21030d.
Yamada et al., Chem. Abst. 1977, vol. 87, No. 202112v.

*Primary Examiner*—Henry R. Jiles
*Assistant Examiner*—Natalia Harkaway
*Attorney, Agent, or Firm*—Daniel T. Szura; Harry E. Westlake, Jr.

[57] ABSTRACT

A process for resolving a mixture of α-fluoromethylhistidine enantiomers is described. The process features use of an ester derivative of α-fluoromethylhistidine. Novel diastereoisomer salts of said derivative are also disclosed.

2 Claims, No Drawings

ACID ADDITION SALTS OF N-TRITYL-α-FLUOROMETHYLHISTIDINE ENANTIOMER DERIVATIVES

BACKGROUND OF THE INVENTION

The invention is concerned with enantiomers of α-fluoromethylhistidine and a process for their preparation from a mixture thereof.

α-Fluoromethylhistidine is disclosed in Great Britain Pat. No. 2,001,626 and South African Pat. No. 78,312; the Great Britain Patent also teaches a specific process for resolution of racemic mixtures. This process however is not useful to resolve (±)-α-fluoromethylhistidine.

A process for resolving a mixture of α-fluoromethylhistidine enantiomers has been discovered.

SUMMARY OF THE INVENTION

A process for resolving a mixture of enantiomers of α-fluoromethylhistidine using an ester derivative of α-fluoromethylhistidine and diastereomer salts of said derivative.

DESCRIPTION OF THE PREFERRED EMBODIMENTS

An embodiment of the present invention is a process for resolving a mixture of enantiomers of α-fluoromethylhistidine of the formula

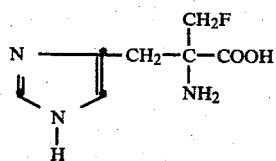

which comprises
a. treating a mixture of enantiomers of $N_{im}$-trityl-α-fluoromethylhistidine alkyl ester of the formula

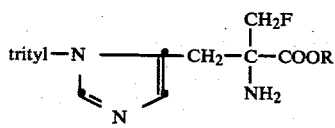

wherein R is $C_1$–$C_3$ alkyl, and preferably methyl, with an enantiomer of α-bromocamphor-π-sulfonic acid in an ethyl acetate preferably ethyl acetate/water, reaction medium,
b. separating the diastereomer salt of compound II/α-bromocamphor-π-sulfonic acid from the reaction mixture
c. recovering a formula II enantiomer by neutralizing said salt and
d. hydrolyzing said formula II enantiomer to obtain the corresponding formula I enantiomer. Trityl is the triphenylmethyl group, $-C(C_6H_5)_3$.

The resolution process is carried out in an ethyl acetate reaction medium. The preferred medium is ethyl acetate with a small amount of water. The volume ratio of ethyl acetate:water may be varied. It may range from about 500:1 to about 10:1, preferably from 250:1 to about 20:1 and more preferably from about 125:1 to about 30:1.

The ratio of formula II:α-bromocamphor-π-sulfonic acid used in the resolution process is also varied. Generally, a molar ratio of formula II:α-bromocamphor-π-sulfonic acid of about 1:1 is used.

The d-α-bromocamphor-π-sulfonic acid is used to obtain the d-α-bromocamphor-π-sulfonic acid.(S) (−)-$N_{im}$-trityl-α-fluoromethylhistidine methyl ester diastereomer salt; the l-α-bromocamphor-π-sulfonic acid is used to obtain the l-60 -bromocamphor-π-sulfonic acid.(R) (+)-$N_{im}$-trityl-α-fluoromethylhistidine methyl ester diastereomer salt. The individual (S) (+) or (R) (−)-α-fluoromethylhistidine enantiomer is recovered from the appropriate diastereomer salt by neutralizing with a suitable neutralizing agent e.g. dilute NaOH, or aqueous $NaHCO_3$ and subsequently hydrolyzing the $N_{im}$trityl alkyl ester of α-fluoromethyl histidine isomer, using conventional techniques e.g. refluxing with an aqueous solution of a hydrohalide such as HCl or HBr.

The (S) (−)-α-fluoromethylhistidine is active as a histidine decarboxylase inhibitor and is useful, for example, for (a) treating ulcers in humans at daily dosages, preferably administered orally, ranging from about 5–50 mg/kg or (b) treating allergic conditions at the dosage ranges indicated above (oral or parenteral administration), in a suitable dosage form. The ointment of (S) (−)-α-fluoromethylhistidine, that is the R(+) ointment, is devoid of such activities.

The following examples illustrate a resolution process of the present invention. The temperatures are centigrade unless otherwise indicated.

EXAMPLE 1

A. Preparation of (±)-methyl α-fluoromethylhistidinate 1,5-naphthalene disulfonate Into a Fisher-Porter tube there was charged 5 g of (±) α-fluoromethylhistidine hydrochloride, 100 ml of methanol, 45 ml of methyl orthoformate and 9.7 g of naphthalene-1,5-disulfonic acid. The tube was sealed and heated in a steam bath overnight. The tube was cooled in an ice bath and the crystalline product (naphthalene-1,5 disulfonic acid salt of α-fluoromethylhistidine) was filtered and returned to the Fisher-Porter tube. Methanol (120 ml), methyl orthoformate (55 ml), and naphthalene-1,5 disulfonic acid (9.4 g) were added, the tube sealed and heated overnight in a steam bath, then cooled in an ice bath for ca. 5 hours. The crystals of (±)-methyl α-fluoromethylhistidinate 1,5-naphthalene disulfonate formed were filtered, washed with cold methanol and diethyl ether and dried in vacuo.

B. Preparation of (±)-methyl $N_{im}$ trityl α-fluoromethylhistidinate (±)-Methyl α-fluoromethylhistidinate-1,5-naphthalene disulfonate (490 mg) was added into 5 ml of methylene dichloride, trityl chloride (586 mg) and triethylamine (0.6 ml) was added. After stirring overnight at room temperature, it was filtered, the filtrate was extracted with water, then the organic phase was dried over $MgSO_4$ and evaporated in vacuo. The residue represented the N,N-ditrityl derivative of (±)methyl α-fluoromethylhistidinate. For selective detritylation first an HCl solution of diethyl ether was prepared by introducing 1.2 g of HCl gas into 13 g of diethyl ether. The ditrityl compound was suspended in 15 ml of diethyl ether and the above HCl-diethyl ether solution was added into it. The mixture was heated to reflux under stirring for 1 hour, cooled filtered and washed with diethyl ether, to give 480 mg of hydrochloride of (±)

methyl-$N_{im}$-trityl-α-fluoromethylhistidinate. 300 mg of this product were suspended in $CH_2Cl_2$, saturated aqueous $NaHCO_3$ solution was added and the mixture was stirred for a few minutes. The separated $CH_2Cl_2$ layer was treated again with $NaHCO_3$, dried over $MgSO_4$, then evaporated in vacuo to give an oil which crystallized from tetrahydrofuran, to give the tetrahydrofuranate of (±) methyl $N_{im}$trityl α-fluoromethylhistidinate, mp 129°–131°. According to C-H-N-F analysis and PMR spectrum, this compound is a tetrahydrofuran complex of methyl $N_{im}$trityl α-fluoromethylhistidinate, containing 0.8 mol of tetrahydrofuran.

C. Preparation of d-α-Bromocamphor-π-sulfonic acid from $NH_4$ salt 72.3 g of d-α-Bromocamphor-π-sulfonic acid $NH_4$ salt (Aldrich, Catalog No. B-6,000-2) was dissolved in 450 ml of water, charcoaled with 3 g of DARCO-G-60, then charged onto a cation-exchange resin column (300 ml of AG-50-X4, 100–200 mesh) in the H+ form. The effluent was collected and evaporated in vacuo to give a solid product, with the approximate composition of a sesquihydrate of d-α-bromocamphor-π-sulfonic acid.

D. Preparation of (S) (−) Methyl-$N_{im}$-trityl α-fluoromethylhistidinate (±)-Methyl $N_{im}$-trityl α-fluoromethylhistidinate tetrahydrofuran complex (27 g) and d-α-bromocamphor-π-sulfonic acid sesquihydrate (18.3 g) were added into 650 ml of ethyl acetate with stirring. After 10 minutes of stirring, 0.7 g of seed crystals of the salt of (S) (−)methyl $N_{im}$ trityl α-fluoromethylhistidinate with d-α-bromocamphor-π-sulfonic acid were added, followed by 13 ml of water. The stirring was stopped after about one minute. After 2 hours standing at room temperature, the crystals formed were filtered and washed with ethyl acetate (2×50 ml). After drying in vacuo, 20.8 g (99% of theory) of (S) (−)-methyl $N_{im}$trityl α-fluoromethylhistidinate.d-α-bromocamphor-π-sulfonic acid.$H_2O$ salt were obtained. This salt was purified by recrystallization from 1800 ml of ethyl acetate, seeded with 0.5 g of optically pure salt. After standing overnight, the crystals separated were collected, washed with ethyl acetate (2×200 ml) and dried in vacuo at 60° C.; 14.6 g of optically pure salt (monohydrated) were obtained, overall yield 69% of theory.

E. Preparation of (S) (−) methyl $N_{im}$-trityl fluoromethylhistidinate

Seventy and 8/10 g of the optically pure salt, obtained as described above, were suspended with 300 ml of dichloromethane and under stirring, 200 ml of 4% aqueous $NaHCO_3$ solution were added. After separation of the 2 layers, the lower layer was extracted 3 more times with $NaHCO_3$ solution; then it was dried over $MgSO_4$ and evaporated in vacuo to dryness. 200 ml of diethyl ether were added to the residue to cause crystallization. The crystals were filtered, washed with ether and dried in vacuo. 98% yield (theory) of (S) (−) methyl $N_{im}$-trityl α-fluoromethylhistidinate was obtained. $[\alpha]_D$ in $CHCl_3$: −15.3°.

The seed crystals mentioned in step D. of this example were obtained as follows: To a solution of 19,8 g of (±) methyl $N_{im}$ trityl α-fluoromethylhistidinate tetrahydrofuranate in 350 ml of ethyl acetate 12 g of d-α-bromocamphor-π-sulfonic acid was added. After stirring one hour, the small amount of precipitate was filtered off and 3 ml water were added to the mother liquor. After 4 hours stirring, the crystals formed were filtered and recrystallized from a mixture of ethyl acetate (600 ml) and water (6 ml). After standing overnight at room temperature, needles were formed. This salt (needles) was filtered and recrystallized 2 more times from ethyl acetate-water (100:1, vol/vol).

F. Preparation of (S)-(+)-α-fluoromethylhistidine dihydrochloride

Thirty-eight and 2/10 g of (S) (−) methyl-$N_{im}$-trityl α-fluoromethylhistidinate was added to 600 ml of conc. aq. HCl; the mixture was stirred and heated under a reflux condenser at 95° C. (oil bath). (Caution: Strong foaming at the beginning) After 6 hours heating, the mixture was aged overnight at room temperature, filtered, washed with water and the filtrate was evaporated in vacuo to give (S) (+)-α-fluoromethylhistidine dihydrochloride; for purification, this was dissolved in 110 ml of methanol, filtered and while boiling hot, 170 ml of isopropanol was added to the filtrate; after aging it in the icebox for 3 days, the crystals were filtered and dried in vacuo; these crystals represented optically pure (S) (+)-α-fluoromethylhistidine dihydrochloride; $[\alpha]_D^{23}$: +17.3° (c, 2.52 in trifluoroacetic acid:water mixture, 1:1); mp 217°–219° C., with decomposition. Single crystal X-ray diffraction analysis affirms the assigned (S) absolute configuration. The free base (S) (−)-α-fluoromethylhistidine $[[\alpha]_D^{23}$: −15.7° (c, 2 in $CHCl_3$)] was obtained from this salt by conventional neutralization.

When step D. was carried out using dry ethyl acetate with no water being added, an (S) methyl $N_{im}$-trityl-α-fluoromethylhistidinate.2 d-α-bromocamphor-π-sulfonic acid salt[1] was obtained in only 6–7% yield. Treatment of this salt with aqueous $NaHCO_3$/ethyl ether followed by appropriate extraction, drying and evaporation yielded (S)(−)methyl $N_{im}$-trityl-α-fluoromethylhistidinate, $[\alpha]_D$ in $CDCl_3$=−14.3°.

[1] This salt differs from the salt disclosed in Example 1D because (1) it contains 1 mole of said histidinate and 2 moles of the sulfonic acid and (2) it is not hydrated.

EXAMPLE 2

Employing substantially the same procedure as described in Example 1, but utilizing the (−) rotating isomer of the resolving agent (that is, 1-α-bromocamphor-π-sulfonic acid) one obtains (R) (−)α-fluoromethylhistidine dihydrochloride.

The reaction described in Example 1 steps A. and B. is illustrated by the following equations:

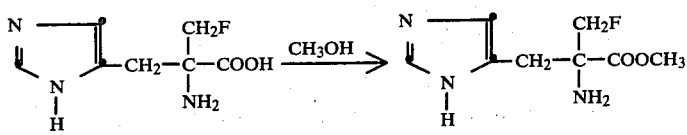

-continued
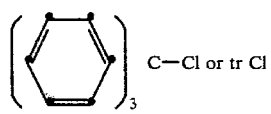
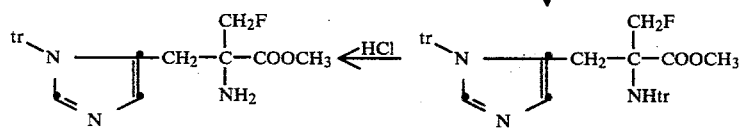
What is claimed is:
1. (S) (−)-N$_{im}$-trityl-α-fluoromethylhistidine methyl ester.d-α-bromocamphor-π-sulfonic acid salt.
2. (S) (−)-α-N$_{im}$-trityl-α-fluoromethylhistidine methyl ester.2 d-α-bromocamphor-π-sulfonic acid salt.
3. S-(−) N$_{im}$ trityl-fluoromethylhistidine methyl ester.d-α-bromocamphor-π-sulfonic acid.H$_2$O salt.
* * * * *